(12) United States Patent
Lehmann et al.

(10) Patent No.: US 7,959,858 B2
(45) Date of Patent: Jun. 14, 2011

(54) PRODUCTS AND METHOD FOR THE DECONTAMINATION OF PRIONS

(75) Inventors: Sylvain Lehmann, Castelnau-le-Lez (FR); Jérôme Solassol, Montpellier (FR)

(73) Assignee: Centre National de la Recherche Scientifique (C.N.R.S.), Paris Cedex (FR)

( * ) Notice: Subject to any disclaimer, the term of this patent is extended or adjusted under 35 U.S.C. 154(b) by 1098 days.

(21) Appl. No.: 11/597,595

(22) PCT Filed: May 24, 2005

(86) PCT No.: PCT/FR2005/001283
§ 371 (c)(1),
(2), (4) Date: Jan. 9, 2007

(87) PCT Pub. No.: WO2005/118762
PCT Pub. Date: Dec. 15, 2005

(65) Prior Publication Data
US 2008/0075630 A1    Mar. 27, 2008

(30) Foreign Application Priority Data
May 24, 2004   (FR) ...................................... 04 05581

(51) Int. Cl.
*A61L 2/18* (2006.01)

(52) U.S. Cl. ........................................................ 422/28

(58) Field of Classification Search ........................ None
See application file for complete search history.

(56) References Cited

U.S. PATENT DOCUMENTS

| 2004/0005304 A1 | 1/2004 | Brudnak |
| 2005/0202491 A1* | 9/2005 | Nelson et al. ................. 435/6 |

FOREIGN PATENT DOCUMENTS

| DE | 44 41 483 | 4/1996 |
| WO | 03/092745 | 11/2003 |

OTHER PUBLICATIONS

McMahon et al., "Cleavage of the Amino Terminus of the Prion Protein by Reactive Oxygen Species", Nov. 1, 2000, Biological Chemistry 276, pp. 2286-2291.*
Hijazi et al., "Copper binding to PrPC may inhibit prion diseas propagation", Oct. 24, 2003, Brain Research 993, pp. 192-200.*
International Search Report for PCT/FR2005/001283 mailed Nov. 4, 2005 (English and French).
Nelson et al, U.S. Appl. No. 60/550,749, filed March 5, 2004, claimed as benefit application of US 2005/0202491 A1, published Sep. 15, 2005.

* cited by examiner

*Primary Examiner* — Walter D Griffin
*Assistant Examiner* — Timothy Cleveland
(74) *Attorney, Agent, or Firm* — Nixon & Vanderhye P.C.

(57) ABSTRACT

The invention relates to the use of Cu and the derivatives thereof, for the decontamination of prions, especially for decontaminating medical devices or medical surgical devices at risk, for decontaminating work surfaces, and for decontaminating any potentially infectious compound.

18 Claims, No Drawings

PRODUCTS AND METHOD FOR THE DECONTAMINATION OF PRIONS

This application is the US national phase of international application PCT/FR2005/001283 filed 24 May 2005, which designated the U.S. and claims priority to FR 0405581 filed 24 May 2004, the entire content of each of which is hereby incorporated by reference.

The invention relates to products and methods for the decontamination of products and equipment infected with unconventional transmissible agents (UTA) responsible for transmissible subacute spongiform encephalopathies.

More specifically, the invention concerns the decontamination of products and equipment infected with prions which accumulate mainly in the brain of the host, more particularly with an abnormal isoform, $PrP^{sc}$ (standing for $PrP^{scrapie}$) which results from a conformational modification of a protein $PrP^c$ (cellular PrP) encoded by the host.

The appearance of a new variant of Creutzfeldt-Jakob disease in Great Britain and its possible link with bovine spongiform encephalopathy raised the possibility of the contagiousness of the disease, in particular via infected products of animal origin, especially via foods and via contaminated medical or surgical equipment.

In fact, the current techniques for disinfection and sterilization do not make it possible easily to destroy prions, which are resistant to the majority of the methods normally used. Administrative directives have laid down the rules to be followed in this regard, but they are very awkward to implement and onerous and they necessitate the use of toxic substances.

In the light of this situation, the inventors sought compounds enabling simple and effective decontamination from the pathological agent, usable on a great majority of surfaces and medical and surgical equipment. Their studies have demonstrated the efficacy of certain metal derivatives in this regard.

The purpose of the invention is thus the use of such compounds for prion decontamination.

It also concerns a method for the treatment of infected equipment and products comprising the use of these compounds.

The invention also concerns the use of Cu and of derivatives thereof, for prion decontamination.

According to a supplementary provision of the invention, these derivatives are used with $H_2O_2$.

Preferably, the metal derivative is $CuSO_4$.

The compound or compounds used according to the invention are advantageously in the form of aqueous solutions.

The study of the action of these derivatives on the decontamination from the pathogenic agents responsible for prion diseases demonstrated their great efficacy for decontaminating infected products or equipment.

Advantageously, these are moreover non-toxic, biodegradable and readily manipulable compounds.

The invention thus equally concerns a process for decontamination of products or equipment infected with pathogenic agents responsible for prion diseases, characterized in that it comprises placing them in contact with at least one compound such as defined above or with a solution containing it, and if necessary with $H_2O_2$.

In a preferred mode of implementation of the invention, the metal derivative is $CuSO_4$.

The decontamination treatment is preferably carried out with a solution containing said compound at a level of at least 500 μM, especially from 500 to 1000 μM.

$H_2O_2$, when it is used, is present in the solutions at a level of about 50 mM.

Satisfactory results are obtained by operating at ambient temperature, for a period of the order of 15 to 60 mins, in particular for about 30 mins.

This compound or these compounds and solutions thereof thus are of great interest in the context of hospital use, where they enable, in particular, decontamination of medical or medical-surgical devices at risk, such as multiple use equipment, such as endoscopes, probes (dialysis), or also decontamination of work surfaces, such as a draining board or floor, also at risk.

Said compounds or solutions thereof are also used in particular for decontaminating for example an infectious material of cerebral origin and biological products originating from subjects who are carriers of infectious forms of Creutzfeldt-Jakob disease. The invention also concerns the use of said compounds and of solutions thereof for decontaminating products originating from the blood or biological material used in transplants.

Advantageously, these compounds and solutions have been found to be effective on the prion strain linked with BSE (transmissible bovine spongiform encephalitis or mad cow disease). They are applicable to all types of prion whatever the strain and origin of the agent may be.

They are also advantageously usable in the context of an agricultural/food application, especially for the decontamination of any potentially infectious compound and in particular animal meal or other contaminated products of animal origin. Applications of interest also include the decontamination of premises, such as abattoirs, with areas and equipment at risk of being in contact with the infectious agents. In particular, those deriving from ruminants may be mentioned.

Other characteristics and advantages of the invention are given in the examples that follow, wherein reference is made to FIGS. 1 and 2, which represent, respectively:

EXAMPLE 1

Prion Decontamination Solution Containing $CuSO_4$ and $H_2O_2$ a) Study of the action of copper associated with $H_2O_2$ on the degradation of the $PrP^{sc}$ present in infectious brain homogenates of mice.

Solutions of $CuSO_4$ and of $H_2O_2$ at different concentrations are added to samples consisting of infectious extracts of murine brain homogenates and are left in contact for about 30 mins at ambient temperature.

The samples are then deposited on a polyacrylamide SDS-PAGE gel after adjustment of the protein concentrations and digestion with proteinase K (PK) at a concentration of 1 mg of PK per 50 mg of protein. The presence of $PrP^{sc}$ is revealed by Western blotting.

The results obtained are illustrated by FIG. 1. It can be seen that at a concentration of 100 μM of $CuSO_4$ and 50 mM of $H_2O_2$, the infectious samples display decreased levels of $PrP^{sc}$. At a concentration of 500 μM of $CuSO_4$ and 50 mM of $H_2O_2$, the level of $PrP^{sc}$ present in the infectious homogenates becomes undetectable in Western blotting (tracks 7 and 8). At this concentration, the effect is potentiated by the action of $H_2O_2$.

With the use of higher doses of $CuSO_4$ from 1 mM to 10 mM, the $PrP^{sc}$ signal can be made to disappear with copper alone and $H_2O_2$ is no longer necessary.

These results are confirmed on repeating these experiments on homogenates deriving from the brains of mice infected with the 22 L prion strain. Similar results have been obtained on homogenates deriving from the murine Chandler strain and BSE, which shows that the decontaminating effect is not strain-dependent.

b) Study of the infectivity of infectious brain homogenates treated with a high concentration of copper in vitro.

22 L brain homogenates were treated for about 30 mins with different concentrations of $CuSO_4$ with and without $H_2O_2$ at different concentrations.

These homogenates are dialyzed, then deposited onto cells of murine neuroblastomas having the capacity to replicate the infectious agent.

Untreated brain homogenates are used as the control.

A Western blot is performed after 6 passages on the cell lysates and after digestion with PK, in order to test for the presence of $PrP^{sc}$ signifying that the samples tested still remain infectious.

The results obtained are given in FIG. 2. It can be seen that the infection is decreased by the treatment.

EXAMPLE 2

Tests In Vivo

A confirmation of these results observed in vitro has been effected. Infectious 22 L brain homogenates were treated in particular with 500 μM of $CuSO_4$ and 100 mM of $H_2O_2$. The homogenates, treated or untreated, were inoculated into mice by the intracerebral route. The control animals inoculated with the untreated homogenates all fell ill in 168 days±2 days. Certain animals inoculated with the treated homogenates are still alive after more than 300 days. This result demonstrates that a reduction of at least 7 powers of ten in the infectious titer can be obtained by this decontamination method.

EXAMPLE 3

Decontamination of Surgical Equipment

Equipment such as endoscopes is immersed in a solution containing 1 mg of $CuSO_4$ for 20 mins. The tests performed to identify the presence of prions after this treatment were found to be negative.

EXAMPLE 4

Study of the Efficacy of Decontamination

The data concerning the efficacy of decontamination tested in vivo after inoculation into the mouse are given below. For this, control and decontaminated brain homogenates were intracerebrally inoculated into the mouse (C57B1).

The survival times of the mice are as follows:

1) Inoculation of control infectious homogenates: 167.6±0.5 days.

2) Homogenates treated with $CuSO_4$ (0.5 mM, 30 mins, ambient temperature): 200.2±8.9 days.

3) Homogenates treated with $CuSO_4$ (1 mM, 30 mins, ambient temperature): 217.2±13.4 days.

4) Homogenates treated with $CuSO_4$ (1 mM)+$H_2O_2$ (100 mM, 30 mins, ambient temperature): 266.4±15.6 days.

In the light of these incubation periods under these different conditions and a titration curve for the infectious agent effected on these mice, it can be estimated that the decontamination obtained is greater than $10^4$ in the homogenates treated just with $CuSO_4$ and greater than $10^5$ in the homogenate treated with $CuSO_4$+$H_2O_2$.

The invention claimed is:

1. A method for decontamination of products or equipment contaminated with pathogenic agents responsible for prion diseases, said method consisting essentially of contacting said products or equipment with a decontaminant solution containing at least one of Cu and a Cu derivative.

2. The method of claim 1, wherein said at least one of Cu and a Cu derivative is present in said solution at a concentration of at least 500 μM.

3. The method of claim 2 wherein said concentration is in the range of from 500 to 1000 μM.

4. A method for decontamination of products or equipment infected with pathogenic agents responsible for prion diseases, said method consisting essentially of contacting said products or equipment with a decontaminant solution containing at least one of Cu and a Cu derivative, and with $H_2O_2$.

5. The method of claim 4 wherein said $H_2O_2$ is present in a solution at a concentration of about 50 mM.

6. The method of claim 1, wherein said Cu derivative is $CuSO_4$.

7. The method of claim 1 wherein said products or equipment are medical devices, medical-surgical devices or work surfaces.

8. The method of claim 7 wherein said products or equipment are an endoscope, a draining board or a floor.

9. The method of claim 1 wherein said products are animal meal or other contaminated products of animal origin.

10. A method for decontamination of products or equipment infected with pathogenic agents responsible for prion diseases, said method consisting of contacting said products or equipment with a decontaminant solution containing at least one of Cu and a Cu derivative.

11. The method of claim 10, wherein said at least one of Cu and a Cu derivative is present in said solution at a concentration of at least 500 μM.

12. The method of claim 11 wherein said concentration is in the range of from 500 to 1000 μM.

13. A method for decontamination of products or equipment infected with pathogenic agents responsible for prion diseases, said method consisting of contacting said products or equipment with a decontaminant solution containing at least one of Cu and a Cu derivative, and with $H_2O_2$.

14. The method of claim 13 wherein said $H_2O_2$ is present in a solution at a concentration of about 50 mM.

15. The method of claim 10, wherein said Cu derivative is $CuSO_4$.

16. The method of claim 10 wherein said products or equipment are medical devices, medical-surgical devices or work surfaces.

17. The method of claim 16 wherein said products or equipment are an endoscope, a draining board or a floor.

18. The method of claim 10 wherein said products are animal meal or other contaminated products of animal origin.

* * * * *